US012139516B2

United States Patent
Cagnac et al.

(10) Patent No.: US 12,139,516 B2
(45) Date of Patent: Nov. 12, 2024

(54) PURIFICATION OF PHYCOBILIPROTEINS

(71) Applicant: FERMENTALG, Libourne (FR)

(72) Inventors: Olivier Cagnac, Libourne (FR); Axel Athane, Carbon-Blanc (FR); Julien Demol, Les Billaux (FR)

(73) Assignee: FERMENTALG, Libourne (FR)

( * ) Notice: Subject to any disclaimer, the term of this patent is extended or adjusted under 35 U.S.C. 154(b) by 333 days.

(21) Appl. No.: 16/497,510

(22) PCT Filed: Mar. 30, 2018

(86) PCT No.: PCT/EP2018/058294
§ 371 (c)(1),
(2) Date: Sep. 25, 2019

(87) PCT Pub. No.: WO2018/178334
PCT Pub. Date: Oct. 4, 2018

(65) Prior Publication Data
US 2020/0115423 A1  Apr. 16, 2020

(30) Foreign Application Priority Data

Mar. 30, 2017 (FR) .................................. 1752674

(51) Int. Cl.
*C07K 14/405* (2006.01)
*A23L 5/46* (2016.01)
*C07K 1/12* (2006.01)
*C07K 1/14* (2006.01)
*C12N 1/12* (2006.01)

(52) U.S. Cl.
CPC .............. *C07K 14/405* (2013.01); *A23L 5/46* (2016.08); *C07K 1/145* (2013.01); *C12N 1/12* (2013.01)

(58) Field of Classification Search
None
See application file for complete search history.

(56) References Cited

FOREIGN PATENT DOCUMENTS

| CN | 101343310 A | 1/2009 |
| CN | 102329381 A | 1/2012 |
| CN | 102731645 A | 10/2012 |
| CN | 106190853 A | 12/2016 |
| JP | S626691 A | 1/1987 |
| JP | H06271783 A | 9/1994 |
| JP | 2004027041 A | 1/2004 |
| RU | 2320195 C | 3/2008 |
| WO | WO2005/065697 A1 | 7/2005 |
| WO | WO2015/090697 A1 | 6/2015 |
| WO | WO2016/099261 A1 | 6/2016 |
| WO | WO2017/050917 A1 | 3/2017 |
| WO | WO2017/050918 A1 | 3/2017 |
| WO | WO2017/093345 A1 | 6/2017 |

OTHER PUBLICATIONS

WO 2005065697 translated copy, 11 pages. (powered by EPO and Google) (obtained from the internet on Jan. 10, 2022). (Year: 2005).*
Thermo Scientific Smart Notes Water Purification 2016: 2 pages (Year: 2016).*
Cruz de Jesus et al. "Methods for Extraction, Isolation and Purification of C-phycocyanin: 50 years of Research in Review", 2016, Int J Food Nutr Sci, vol. 3, No. 1, pp. 275-284.
Eisele et al., "Studies on C-phycocyanin from Cyanidium caldarium, a eukaryote at the extremes of habitat", Biochemica et Biophysica Acta 1456, 2000, pp. 99-107.
Eriksen "Production of phycocyanin—a pigment with applications in biology, biotechnology, foods and medicine", Appl Microbiol Biotechnol., 2008, vol. 80, pp. 1-14.
Kao et al., "Physical-Chemical Properties of C-Phycocyanin Isolated from an Acido-Thermophilic Eukaryote, Cyanidium caldarium", Biochem. J., 1975, vol. 147, pp. 63-70.
Moon et al. "Isolation and Characterization of Thermostable Phycocyanin from Galdieria Sulphuraria", Korean Journal of Chemical Engineering, 2014, vol. 31, No. 3, pp. 490-495.
Sorensen et al. "Purification of the photosynthetic pigment C-phycocyanin from heterotrophic Galdieria sulphuraria", J Sci Food Agric., 2013, vol. 93, No. 12, pp. 2933-2938.
Yan et al. "Single-step chromatography for simultaneous purification of C-phycocyanin and allophycocyanin with high purity and recovery from Spirulina", J. Appl. Phycol, 2011, vol. 23, pp. 1-6.
Rahman et al. "Thermostable phycocyanin from the red microalga *Cyanidioschyzon merolae*, a new natural blue food colorant", J. Appl. Phycol., 2016, vol. 23. No. 3, pp. 1233-1239.
Schonknecht et al. "Gene Transfer from Bacteria and Archea Facilitated Evolution of an Extremophilic Eukaryote", Science, Mar. 8, 2013, vol. 339, No. 6124, pp. 1207-1209.
Hoogland "Prairie Dogs Disperse When All Close Kin Have Disappeared", Science, Mar. 8, 2013, vol. 339, No. 6124, pp. 1205-1207.
International Search Report from PCT/EP2018/058294; Aug. 31, 2018; Bayrak, Sinasi.
Chaiklahan R. et al. "Stability of phycocyanin extracted from *Spirulina* sp.: Influence of temperature, pH and preservatives", Process Biochemistry, 2012, 47, p. 659-664.
Cizkova M. et al., "The red microalga *Galdieria* as a promising organism for applications in biotechnology", Microalgae from Physiology to Application, IntechOpen, p. 1-17.
Kupka M. et al., "Unfolding of C-phycocyanin followed by a loss or non-covalent chromophore-protein interactions 1. Equilibrium experiments", Biochimica et Biophysica Acta 2008, 1777, p. 94-103.
Böcker L. et al. "Time-temperature-resolved functional and structural changes of phycocyanin extracted from Arthrospira paltensis/Spirulina", Food chemistry 2020, 316, 126374, p. 1-9.
Scheer H. et al. "Conformational studies on C-phycocyanin from Spirulina platensis", Z. Naturforsch, 32c, 513-519, 1977.

* cited by examiner

*Primary Examiner* — Marsha Tsay
(74) *Attorney, Agent, or Firm* — BCF LLP

(57) ABSTRACT

The present invention relates to a novel process for purifying phycobiliproteins, in particular acid-pH-resistant phycobiliproteins, the resulting phycobiliproteins, and the uses thereof.

6 Claims, 4 Drawing Sheets
Specification includes a Sequence Listing.

PURIFICATION OF PHYCOBILIPROTEINS

FIELD OF THE INVENTION

The present invention relates to a novel process for purifying phycobiliproteins, in particular acid-pH-resistant phycobiliproteins, the resulting phycobiliproteins, and the uses thereof.

STATE OF THE ART

The purification of phycobiliproteins of *Galdieria sulphuraria*, in particular C-phycocyanin (C-PC), is much more complex than that of *Arthrospira platensis (Spirulina)* or other cyanobacteria. This is partly due to the composition of the *Galdieria sulphuraria* cell wall, which requires mechanical action to rupture (Sorensen et al., 2013). Mechanical lysis results in the formation of micelles that are only partially removed by ultracentrifugation. The presence of chlorophyll a and dissolved carotenoids in these micelles contributes to increasing the absorbance values at 280 nm (protein-specific UV absorbance) which may explain the low purity levels of C-PC crude extracts compared with *Spirulina* crude extracts (Sorensen et al., 2013). The purity level of the crude extract can therefore be increased by removing micelles and soluble proteins other than phycobiliproteins.

The purification of phycobiliproteins extracted from *Cyanidioschyzon merolae, Cyanidium caldarium, Galdieria sulphuraria* and *Spirulina* by precipitation with ammonium sulphate has already been described in the literature (WO 2016/099261; Eisele et al., 2000; Kao et al. Moon et al., 1975; 2015; Cruz de Jesus et al., 2006) but it is very difficult to apply on an industrial scale because it requires a lot of ammonium sulphate, which poses major problems for the reprocessing of ammonium sulphate and supernatant.

The other purification methods described to obtain a purity level such that chromatographic methods are very expensive to implement.

The invention therefore relates to a process for purifying phycobiliproteins produced by bioreactor culture of phycobiliprotein-producing microorganisms, which is easy to implement and economically suitable for industrial-scale implementation.

In addition, the phycobiliproteins, in particular the phycocyanins, are mixtures of c-phycocyanin and allophycocyanin. Known purification processes do not allow them to be separated in an industrially controlled manner. Purification by precipitation with ammonium sulphate entrains both proteins in an uncontrolled manner, so it may be difficult to obtain a pigment with stable properties. This precipitation method also results in substantial extraction yield losses (Cruz de Jesus et al., 2006).

The invention therefore also relates to the preparation of purified phycobiliproteins, in particular of purified phycocyanin comprising essentially c-phycocyanin or essentially allophycocyanin, in particular of acid-pH-resistant phycobiliproteins of controlled composition in phycocyanins, the resistance to acid pH not requiring the addition of stabilizing agents such as ascorbic acid (WO 2005/065697) or polyphenols (WO 2015/090697).

DISCLOSURE OF THE INVENTION

The invention therefore relates to a process for purifying acid-pH-resistant phycobiliproteins from a crude extract of acid-pH-resistant phycobiliproteins, characterized in that it comprises the steps of a) adjusting the pH of the crude extract of acid-pH-resistant phycobiliproteins to a pH below 6 so as to precipitate organic matter other than acid-pH-resistant phycobiliproteins,
b) recovering the supernatant comprising acid-pH-resistant phycobiliproteins and
c) isolating acid-pH-resistant phycobiliproteins from the supernatant.

The invention also relates to the acid-pH-resistant phycobiliproteins obtained by the process and in particular, acid-pH-resistant phycocyanins comprising a mixture of c-phycocyanin and allophycocyanin, more particularly whose molar ratio of c-phycocyanin to allophycocyanin is at least 2.

DETAILED DESCRIPTION OF THE INVENTION

Figure 1:
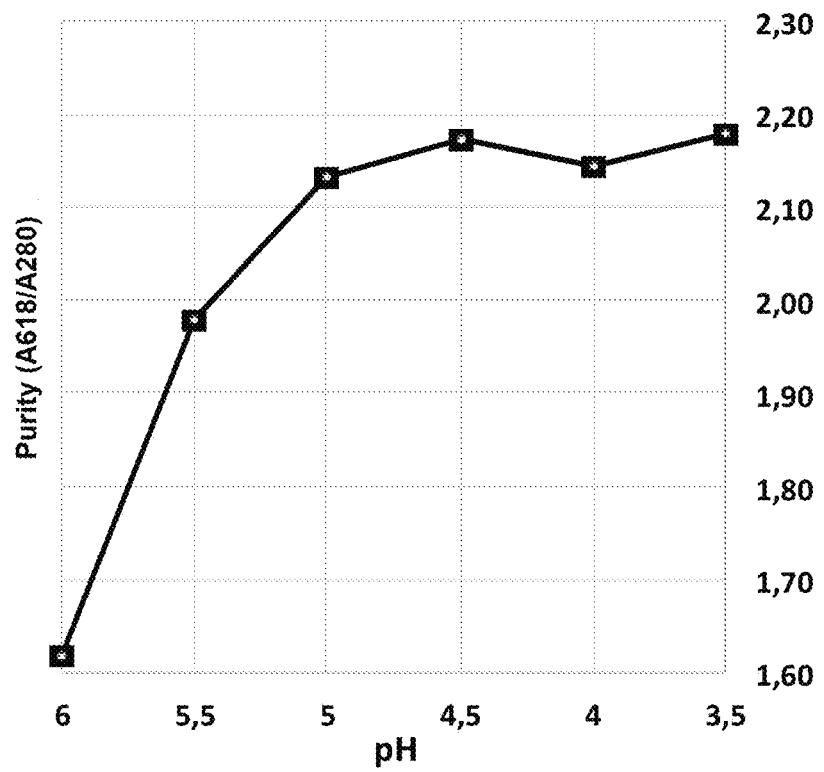
FIG. 1. Increase in the purity index of the crude extract as a function of pH from a lysate of fresh cells.

The invention therefore relates to a process for purifying acid-pH-resistant phycobiliproteins from a crude extract of acid-pH-resistant phycobiliproteins.

The crude extract of phycobiliproteins is generally obtained from cells of microorganisms grown industrially in high-capacity bioreactors, preferably in such a way as to obtain fermentation must with high densities of phycobiliprotein-producing microorganisms (high densities is generally defined as more than 50 g dry matter (DM) per litre of fermentation must, preferentially more than 100 g/L). These culture methods are known to the skilled person and may be carried out in autotrophy, heterotrophy or mixotrophy, in particular described in applications WO 2017/050917, WO 2017/050918 and PCT/EP2016/079325 filed on 30 Nov. 2016. Phycobiliproteins produced by cultured microorganisms must be released after cell lysis. Indeed, microorganism cells contain large quantities of phycobiliproteins (Moon et al., 2015, Sorensen et al., 2013, Eriksen 2008). Consequently, the implementation of the process according to the invention requires first the preparation of an aqueous extract from the fermentation must.

The aqueous extract can be prepared directly from the fermentation must as it is recovered from the reactor at the end of fermentation, possibly with the addition of an appropriate amount of water.

It can be prepared from fresh cells separated from the fermentation must by any separation method well known to the skilled person. It can also be prepared from cells that have been freeze-dried or dried for storage.

According to a preferred embodiment of the invention, the aqueous extract is prepared from fresh cells separated from the fermentation must after culture.

Cell lysis can be carried out by any means of cell lysis known to the skilled person. It can be done while the cells are suspended in water, fermentation must or reconstituted suspension.

According to a preferred embodiment of the invention, cell lysis is carried out on the cells separated from the fermentation must, before they are resuspended.

Preferably, the aqueous extract is obtained from the suspension comprising the lysed cells by separating the solids, by any means of separation known to the skilled person to remove the solid residues of cell lysis, in particular filtration.

This results in an aqueous extract called "crude extract of phycobiliproteins" or "crude extract" which comprises, in addition to the desired phycobiliproteins, in particular acid-pH-resistant phycobiliproteins, other organic materials such as micelles and other water-soluble proteins.

The crude extract of phycobiliproteins can be prepared from fresh lysed cells (directly in the fermentation must or after separation of the fermentation must) or from freeze-dried or dried cells, with cell lysis occurring before or after freeze-drying or drying.

According to a preferred embodiment of the invention, the crude extract is prepared from fresh cells.

The purification process according to the invention consists in separating phycobiliproteins, in particular acid-pH-resistant phycobiliproteins, from other organic materials such as micelles and other water-soluble proteins.

The microorganisms cultivated to produce phycobiliproteins are well known to the skilled person, in particular selected from the group of Cyanophyceae such as *Arthrospira platensis* (*Spirulina*), *Spirulina maxima*, *Synechococcus elongatus*, or the group of Cyanidiophyceae such as *Galdieria sulphuraria*, *Cyanidium caldiarium*, *Cyanidioschyzon merolae*.

Preferably, the phycobiliproteins are acid-pH-resistant phycocyanins. Acid-pH-resistant phycobiliproteins or acid-pH-resistant phycocyanins are defined as phycobiliproteins that resist precipitation at acid pH. According to the invention, acid pH means a pH below 7, advantageously of 6 or less. Advantageously, the acid-pH-resistant phycobiliproteins do not precipitate in aqueous solution at pH levels below 6. They can also be described as either resistant or stable at acid pH.

Of course, the purified phycobiliproteins according to the invention will be more or less stable depending on the acid pH considered. Some will be stable in a pH value range around 6, others will be stable at pH values well below 6. Consequently, acid-pH-resistant phycobiliprotein is also defined as a mixture of phycobiliproteins, the majority of which do not precipitate at a pH below 7, advantageously below 6 or less.

Advantageously, the invention relates to phycobiliproteins stable at pH less than 5, preferentially less than or equal to 4, more preferentially ranging from 4 to 2, even more preferentially less than or equal to 3.5.

Such acid-pH-resistant phycocyanins are known to the skilled person, particularly described in application WO 2016/099261 or application WO 2017/050918. In particular, these are phycocyanins produced by microalgae strains of the genera *Cyanidioschyzon*, *Cyanidium* or *Galdieria*, in particular selected from the species *Cyanidioschyzon merolae* 10D, *Cyanidioschyzon merolae* DBV201, *Cyanidium caldarium*, *Cyanidium daedalum*, *Cyanidium maximum*, *Cyanidium partitum*, *Cyanidium rumpens*, *Galdieria daedala*, *Galdieria maxima*, *Galdieria partita*, *Galdieria sulphuraria*, in particular strains of *Galdieria sulphuraria*, *Cyanidium caldarium* and *Cyanidioschyzon merolae*.

These phycocyanins are a mixture of c-phycocyanin (C-PC) and allophycocyanin (APC).

Advantageously, the apoprotein of C-PC comprises the protein of SEQ ID NO 1 or of SEQ ID NO 2 or a variant thereof. In particular, the apoprotein of the a subunit of C-PC comprises the protein of SEQ ID NO 1 and the apoprotein of the ß subunit of C-PC comprises the protein of SEQ ID NO 2 or variants thereof.

```
SEQ ID 1:
MKTPITEAIA AADNQGRFLS NTELQAVNGR YQRAAASLEA

ARSLTSNAQR LINGAAQAVY SKFPYTSQMP GPQYASSAVG

KAKCARDIGY YLRMVTYCLV VGGTGPMDEY LIAGLEEINR

TFDLSPSWYV EALNYVKSNH GLSGQAANEA NTYIDYAINA LS

SEQ ID 2:
MLDAFAKVVA QADARGEFLS NTQLDALSKM VSEGNKRLDV

VNRITSNASA IVTNAARALF SEQPQLIQPG GNAYTNRRMA

ACLRDMEIIL RYVSYAIIAG DSSVLDDRCL NGLRETYQAL

GVPGASVAVG VEKMKDSAIA IANDPSGITT GDCSALMAEV

GTYFDRAATA VQ
```

Also advantageously, the a subunit of said APC comprises SEQ ID NO 3 or variants thereof and the apoprotein of the ß subunit of said APC comprises SEQ ID NO 4 or variants thereof.

```
SEQ ID 3:
MSLISQIINT ADEELRYPNG GELSTLIYFF NTANTRINII

NKLKEREKDI IQNASKKLFQ LHPEYVSSGG NASGPKQRAL

CLRDYGWYLR LVTYGILAGD ITPIEKIGII GVKDMYNSLG

VPIIGMYDAI KCLKEASINI FELSEEKDLI IPYFDYLSNA ILS

SEQ ID 4:
MSIVTKSIVN ADAEARYLSP GELDRIKSFV LSGQRRLRIA

QILTDNRERI VKQAGQQLFQ QRPDIVSPGG NAYGEEMTAT

CLRDLDYYLR LVTYGVVAGD ISPIEEIGLE DFMQDAITAV

INTADVQGKY LDNSSIEKLK GYFQTGELRV RAAATIAANA
```

-continued

AGIIKDAVAK SLLYSDITRP GGNMYTTRRY AACIRDLDYY

LRYATYSMLA GDPSILDERV LNGLKETYNS LGVPIGATIQ

SIQAMKEVTS SLV

The apoproteins of C-PC and APC from the same phycocyanin source generally have different isoelectric points. By lowering the pH, it will be possible to at least partially separate C-PC from APC.

Indeed, the inventors found that the more the pH of the crude extract was adjusted downward, the purer the C-PC obtained.

Advantageously, when the phycobiliprotein is an acid-pH-resistant phycocyanin, lowering the pH below the isoelectric point of APC results in a phycocyanin comprising a C-PC/APC mixture with a molar ratio of at least 5, preferentially at least 10, more preferentially at least 15.

Preferably, the pH of the crude extract in step a) is adjusted to a pH below 5. It is thus possible to obtain acid-pH-resistant phycocyanin containing less than 5 mol % APC, preferentially less than 1%, more preferentially less than 0.1% APC, the percentages being expressed in relation to the total sum of APC and C-PC.

In step a), the pH adjustment is done by adding a strong or weak mineral or organic acid in solid or solution form, the amount of acid added being determined by the pH of the crude extract to be treated and the pH value that the skilled person will seek to obtain. Among the mineral acids well known to the skilled person, particular mention may be made of hydrochloric acid and phosphoric acid. Among the organic acids well known to the skilled person, particular mention may be made of acetic acid, citric acid, tartaric acid, lactic acid, preferably citric acid. Mention also may be made of acidic polyphenols such as rosmarinic acid, tannic acid, digallic acid, quercitannic acid, gallotannic acid, acidic tannins such as quercetin, ellagitannins, castalagin, castaline, casuariticin, grandinin, punicaligin punicalin, roburin A, tellimagrandin II, terflavin B, vescaligin, pendunculagin, casuariin, castlin, vescalin, preferably tannic acid. Preferably, the acids used are acids authorized for use in foods, in particular phophoric acid, citric acid or tannic acid.

For step b) of recovering the supernatant comprising acid-pH-resistant phycobiliproteins, any separation method known to the skilled person may be used, in particular by tangential filtration on ceramic membranes or organic membranes such as polyethersulfone hollow fibres. The cut-offs of these filters can be selected to separate molecules of higher or lower molecular weight than the targeted phycobiliproteins.

According to a particular embodiment of the invention, the separation in step b) is done by tangential filtration. This step concentrates and removes some of the proteins other than phycobiliproteins, thus increasing the purity level of the final product.

Step c) of drying/dehydrating acid-pH-resistant phycobiliproteins from the supernatant is done by any method of removing the solvent, in this case water, for example by evaporation at atmospheric pressure or under vacuum. Particular mention may be made of atomization, freeze-drying, zeodratation, infrared drying, or refraction window drying.

In the event of evaporation by heating, the skilled person should take care not to use excessively high temperatures which could cause denaturation of the phycobiliproteins.

It is possible, after recovering the supernatant in step b), to recycle the phycobiliproteins contained in the precipitate. To do this, the residual phycobiliproteins are solubilized in an aqueous solution of acid pH, of about 6, or less, at which pH the impurities remain insoluble while the phycobiliproteins are soluble.

These residual phycobiliproteins are then separated from the impurities and isolated by repeating steps b) and c) of the process. It is an iterative process that can be repeated as many times as necessary. When the conditions used for the process according to the invention allow preferential purification of C-PC, the residual phycobiliproteins are a C-PC/APC mixture enriched in APC.

By recycling the precipitate, phycobiliproteins are obtained comprising a C-PC/APC mixture with a molar ratio of less than 5, in particular less than 4, advantageously in the range of 3 to 0.1.

By repeating steps a) to c) of the process described above, it is possible by an iterative process to exhaust the precipitate of C-PC, which can be added to the previously obtained fractions to enrich their content and also to enrich the residual mixture of phycobiliproteins in APC, with an APC/C-PC ratio of at least 5, preferentially of at least 10, more preferentially of at least 15.

It is this possible to obtain an APC mixture containing less than 5 mol % CPC, preferably less than 1%, more preferentially less than 0.1% CPC, the percentages being expressed in relation to the total sum of APC and C-PC.

These APC isolated from the precipitate can then be further purified by preparative chromatography techniques well known to the skilled person for the production of allophycocyanins which can be used as in the field of medical imaging for example due to these fluorescent properties The invention also relates to acid-pH-resistant phycobiliproteins, in particular phycocyanins, obtainable by the purification process.

The invention also relates to purified acid-pH-resistant phycocyanins comprising a C-PC/APC mixture with a molar ratio of at least 2.

In particular, the invention relates to an acid-pH-resistant phycocyanin which comprises at least 95 mol % C-PC and less than 5 mol % APC, preferentially at least 99 mol % C-PC and less than 1 mol % APC, the percentages being expressed in relation to the total sum of APC and C-PC.

These C-PCs are known to the skilled person and in particular defined above, in particular those whose a subunit of C-PC comprises the protein of SEQ ID NO 1 and the apoprotein of the 13 subunit of C-PC comprises the protein of SEQ ID 2 or variants thereof.

Advantageously, the variants according to the invention have a sequence identity of at least 83% for the a subunits of C-PC, and of at least 82% for the 13 subunits of C-PC.

Preferentially, the variants according to the invention have an identity of at least 90% for the α (SEQ ID NO 1) and 13 (SEQ ID NO 2) subunits.

The invention also relates to a purified phycocyanin enriched in APC obtainable by the process according to the invention.

In particular, the invention relates to purified phycocyanin which comprises a mixture enriched in APC whose C-PC/APC molar ratio is less than 5, in particular 4, advantageously in the range of 3 to 0.1.

According to a particular embodiment of the invention, the mixture enriched in APC has an APC/C-PC ratio of at least 5, preferably of at least 10, more preferably of at least 15.

According to a more specific embodiment of the invention, the phycocyanin consists essentially of APC, with at least 95 mol % APC and less than 5 mol % C-PC, preferably at least 99 mol % APC and less than 1 mol % C-PC, the percentages being expressed in relation to the total sum of APC and C-PC.

These APCs are known to the skilled person and in particular defined above, in particular those whose a subunit of said APC comprises SEQ ID NO 3 or variants thereof and the apoprotein of the 13 subunit of said APC comprises SEQ ID NO 4 or variants thereof.

Advantageously, the variants according to the invention have a sequence identity of at least 83% for the a subunits of APC, and of at least 82% for the 13 subunits of APC.

The skilled person knows how to measure the identity of protein sequences using the usual methods at her disposal, in particular the BLASTP programme.

Similarly, the skilled person knows how to identify variants of said sequences and to verify that they retain the same structural properties by simple stability testing at acid pH, for example by performing a test such as the test presented in Example 3 of application WO 2017/050918.

It is known to the skilled person that a polypeptide can be modified by substitution, insertion and/or deletion of at least one amino acid without substantially modifying its function.

For example, the substitution of an amino acid at a given position by another chemically equivalent amino acid is a known example of sequence variation that does not substantially affect the properties of the protein.

These "conservative" substitutions can be defined as exchanges within the following amino acid groups
  Ala, Ser, Thr, Pro, Gly
  Asp, Asn, Glu, Gln
  His, Arg, Lys
  Met, Leu, Ile, Val, Cys and
  Phe, Tyr, Trp Thus, the variants of the apoproteins of the phycocyanins and/or allophycocyanins according to the invention may comprise from 1 to 30 amino acids different in number compared with the corresponding so-called reference sequence, particularly with regard to the α and/or β subunits of phycocyanin, provided that the variant obtained retains the properties of the reference protein and the homology/identity percentages stated above.

More precisely according to the invention,
  for the variants of the apoproteins of the α subunit of phycocyanins usable in the acid compositions according to the invention, resulting from substitutions, insertions and/or deletions, they may comprise from 1 to 27 amino acids different from the corresponding so-called reference sequence, provided that the variant obtained retains the properties of the reference protein and the identity percentages stated above;
  for the variants of the apoproteins of the β subunit of phycocyanins usable in the acid compositions according to the invention, resulting from substitutions, insertions and/or deletions, they may comprise from 1 to 30 amino acids different from the corresponding so-called reference sequence, provided that the variant obtained retains the properties of the reference protein and the identity percentages stated above;
  for the variants of the apoproteins of the α subunit of allophycocyanins usable in the acid compositions according to the invention, resulting from substitutions, insertions or deletions, they may comprise from 1 to 24 amino acids different from the corresponding so-called reference sequence, provided that the variant obtained retains the properties of the reference protein and the identity percentages stated above;
  for the variants of the apoproteins of the β subunit of the allophycocyanins usable in the acid compositions according to the invention, resulting from substitutions, insertions and/or deletions, they may comprise from 1 to 20 amino acids different from the corresponding so-called reference sequence, provided that the variant obtained retains the properties of the reference protein and the identity percentages stated above.

Very particularly according to the invention, and whatever the reference sequence considered (α and/or β subunit of phycocyanin and/or α and/or β subunit of allophycocyanin) the variants of said subunits can advantageously comprise from 1 to 15 amino acids of difference, preferably from 1 to 10 amino acids of difference, in particular 1 or 2 or 3 or 4 or 5 or 6 or 7 or 8 or 9 or 10 amino acids of difference compared with the corresponding so-called reference sequence, provided that the variant obtained retains the properties of the reference protein and the identity percentages set out above.

Preferably, the invention relates to C-PC whose subunit alpha protein consists of the protein of SEQ ID 1 and the beta subunit protein consists of the protein of SEQ ID 2.

According to another preferred embodiment, the invention relates to APC whose subunit alpha protein consists of the protein of SEQ ID 3 and the subunit beta protein consists of the protein of SEQ ID 4.

Phycobiliproteins are natural dyes mainly used for food colouring.

The invention also relates to the use of acid-pH-resistant phycobiliproteins obtained by the process according to the invention and in particular the acid-pH-resistant phycocyanins defined above as a dye in a food product.

The invention also relates to a composition, in particular a food composition, comprising acid-pH-resistant phycobiliprotein obtained by the process according to the invention and in particular the acid-pH-resistant phycocyanin as defined above.

Such uses and such compositions are known to the skilled person.

Preferentially, the food product or food composition is an acid composition, as defined in application WO 2017/050918.

According to the invention, an acid composition is defined as any composition comprising a mineral or organic acid and phycocyanin. This composition can be liquid, fluid or viscous, pasty or solid with an acid pH and in which the acid-pH-resistant phycocyanin is incorporated.

For aqueous liquid compositions, the pH is measured in the usual way. For non-aqueous liquid compositions or for pasty or solid compositions, the pH is measured after dissolution of the composition in an amount of water sufficient to dissolve the soluble compounds it contains, including mineral or organic acids and phycocyanin.

Advantageously, the composition according to the invention is an aqueous liquid composition, optionally in the form of a gel, or a pasty or solid composition intended to be dissolved in an aqueous solution or in a solid or pasty composition comprising water. According to another advantageous embodiment of the invention, the acid composition is a pasty or solid composition intended to be used and/or stored in a humid environment.

The mineral or organic acids that may be used in the compositions according to the invention are well known to the skilled person. Among the mineral acids, particular mention may be made of carbonic, phosphoric, hydrochloric, sulphuric, perchloric, sulphonic and nitric acids. Among the organic acids, particular mention may be made of citric, lactic, malic, tartaric, succinic acids, advantageously citric acid.

According to the invention, acid food composition means any composition intended for ingestion by humans or animals that falls within the above definition. Nutraceutical acid compositions must be considered as falling within the definition of acid food compositions in the sense of the invention.

The acid food compositions according to the invention are well known to the skilled person. They may include a vehicle that may include structural components associated with active compounds identified for their nutrient contribution or for their properties beneficial to human or animal health. The acid food composition according to the invention may also include food additives such as texturizing agents, flavouring agents, preservatives, all of which are well known to the skilled person. The vehicle may include water and/or protein and/or fat and/or fibre and/or sugar. The components of the vehicle may only have structural properties, but they are generally known for their nutrient contributions.

The acid food composition according to the invention may be ready-to-use or in the form of a food additive that is added to a solid, pasty or liquid preparation to prepare the food that can be ingested.

For food compositions, the acid should preferably be selected from the list of approved dietary acidifying agents, in particular carbonic, phosphoric, citric, malic, tartaric and lactic acids, more particularly citric acid.

Concerning acidic compositions other than food compositions according to the invention, they may be, inter alia, pharmaceutical, veterinary or cosmetic and may further comprise any additives and/or active agents known and used in this type of composition.

In a solid, liquid or pasty acid composition according to the invention, phycocyanin can be incorporated, for example, in powder form. Said acid composition, particularly said acid food composition, may then be in any known usual form such as creams, gels, foams, pastes, etc. Especially for a solid food composition, particular mention may be made of cakes or biscuits, dry cooking foods, powders to be diluted, solid or "jelly" gelatinous compositions, foams etc.

According to the invention, said liquid acid composition may be an aqueous composition in which the phycocyanin is dissolved. It may be in the form of a ready-to-use composition or as a liquid concentrate to be diluted, in particular for ingestion or to be added to a solid food either for its preparation or for ingestion, for example a liquid coating concentrate or "topping" composition which will be placed on a cake to give it its colour. Among these concentrated compositions, mention may be made of syrups, optionally containing alcohol.

The liquid acid composition according to the invention may be of variable viscosity and may or may not include additives such as viscosity agents, gelling agents, and other structuring additives known to the skilled person and customary for the preparation of liquid food compositions.

According to a particular embodiment of the invention, the liquid food composition may be an acidic drink, optionally carbonated. These include sodas, juices, sports drinks, sports drinks, fitness drinks, recovery drinks, etc. The compositions of these drinks are well known to the skilled person and may include, in particular, sugars, mineral salts, food additives, dissolved gas, etc. The drink according to the invention is a usual acid drink in which the dye usually used has been replaced in whole or in part by an acid-pH-resistant phycocyanin according to the invention.

According to the invention, the phycocyanin content in the compositions according to the invention may be in accordance with the practices of the skilled person.

For example, when phycocyanin is used to colour the acid composition, then the phycocyanin content in said composition may be in accordance with the practices of the skilled person as regards colouring.

In a liquid acid composition as defined in the invention, the phycocyanin content may be between 2.5 mg/L and 2500 mg/L, preferentially between 25 mg/L and 300 mg/L.

In a ready-to-use liquid drink composition, the phycocyanin content can generally be between 25 mg/l and 300 mg/L, preferably between 50 mg/L and 100 mg/L.

In a concentrated liquid composition to be diluted for use, such as a syrup, the phycocyanin content can generally be between 250 mg/l and 2500 mg/l, preferentially between 500 mg/L and 1000 mg/L.

In a solid composition, the phycocyanin content can generally be between 0.01 mg/g and 10 mg/g, preferentially between 0.1 mg/g and 5.0 mg/g, very preferentially between 0.25 mg/g and 2.5 mg/g.

EXAMPLES

Example 1. Purification by Acid Precipitation on Fresh Cells

A *Galdieria sulphuraria* cell fermentation must centrifuged and rinsed with an equivalent volume of water is mechanically ground to release the phycobiliproteins in an aqueous phase at pH 6. The ground material is acidified in 0.5 pH unit steps by adding citric acid. At each level, a sample of the mixture is taken and then centrifuged for 10 min at 11,000 g. The supernatant containing the phycobiliproteins is collected and the purity index measured by measuring the ratio of absorbance at 618 nm to the absorbance at 280 nm with a spectrophotometer (Amersham Biosciences Ultra Spec 2100 Pro).

Figure 2:
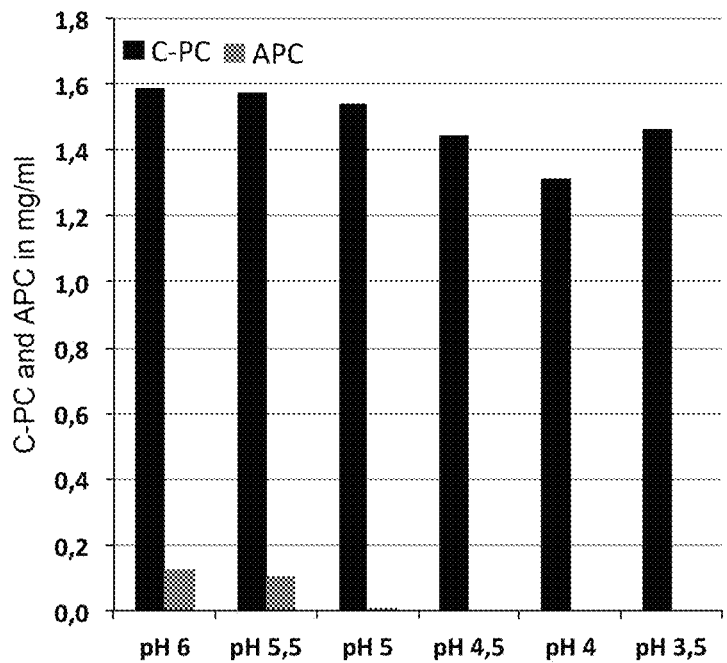
FIG. 2: Measurement of the concentration of C-PC and APC in different crude extracts obtained by centrifugation of a fresh cell lysate at different pH levels. APC concentrations (mg/ml) are shown in grey and C-PC concentrations (mg/ml) in black.
Figure 3:
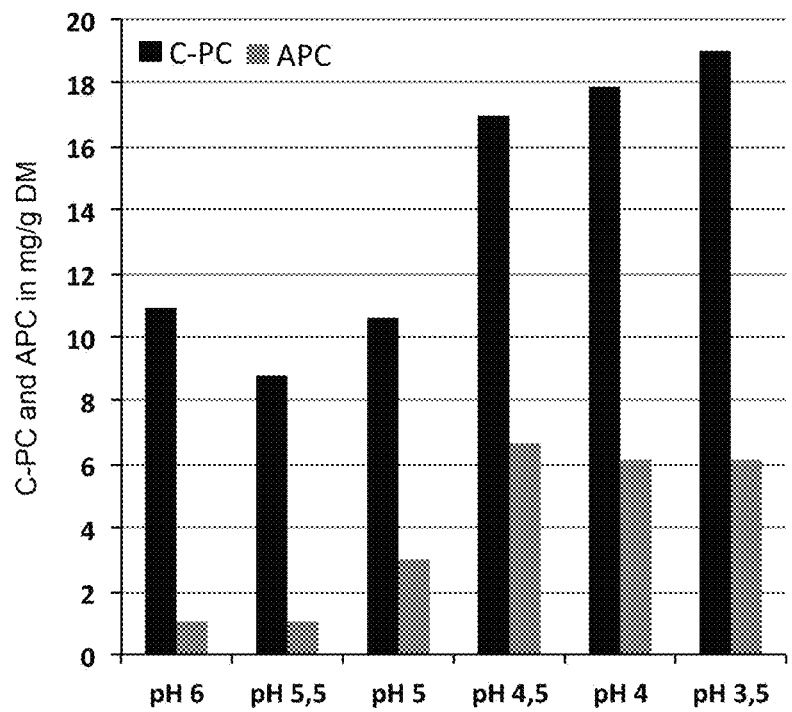
FIG. 3: Measurement of the concentration of C-PC and APC in pellets obtained by centrifugation of a fresh cell lysate at different pH levels. APC concentrations (mg/g DM) are shown in grey and C-PC concentrations (mg/g DM) in black.

It is clear that the lower the pH, the higher the purity index (FIG. 1). This increase in the purity index reflects a decrease in contaminating proteins in the supernatant, while C-PC remains predominantly in the supernatant. Due to its resistance to acid pH there is no substantial loss of C-PC content in the supernatant (FIG. 2). Surprisingly, allophycocyanin (APC) disappears completely from the supernatant at pH values below 5, ending up in the pellet with other precipitated proteins and cell debris (FIG. 3). This pellet also contains C-PC and APC with a higher content of APC (FIG. 3).

Acidification also results in better separation of the liquid and solid phases and a pellet of cell debris and proteins which is more compact and easier to separate from the aqueous phase.

Example 2. Purification by Acid Precipitation on Freeze-Dried and Rehydrated Cells A *Galdieria sulphuraria* cell fermentation must centrifuged and rinsed with an equivalent volume of water is mechanically ground to release the phycobiliproteins in an aqueous phase at pH 6. The ground material is then freeze-dried. The freeze-dried dry matter is suspended in a volume of water equivalent to the initial volume of the must and then acidified in 0.5 pH unit steps by adding citric acid. At each level, a sample of the mixture is taken and then centrifuged for 10 min at 11,000 g. The supernatant containing the phycobiliproteins is collected and the purity index measured by measuring the ratio of absorbance at 618 nm to the absorbance at 280 nm with a spectrophotometer (Amersham Biosciences Ultra Spec 2100 Pro).

Figure 4:
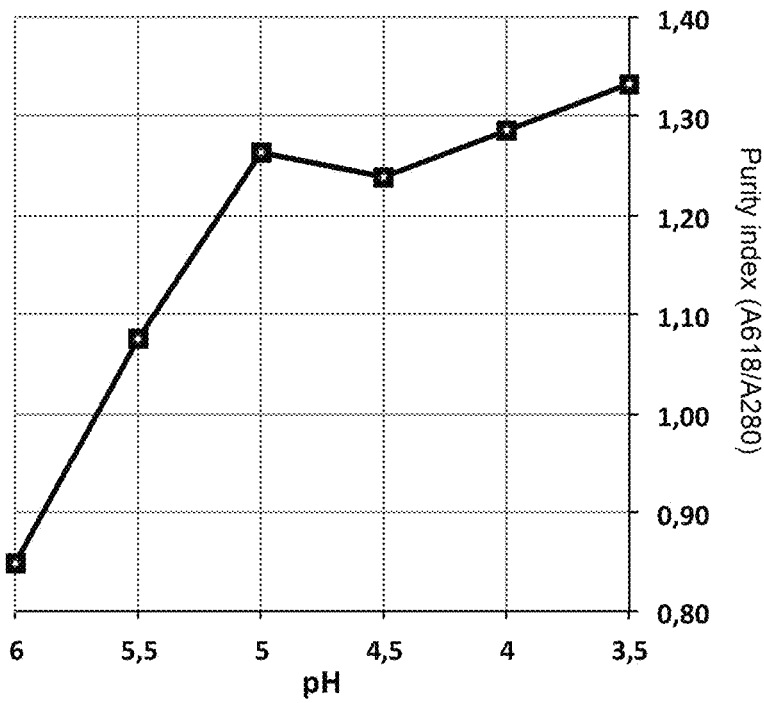
FIG. 4. Increase in the purity index of the crude extract as a function of pH from a lysate of freeze-dried and rehydrated cells.
Figure 5:
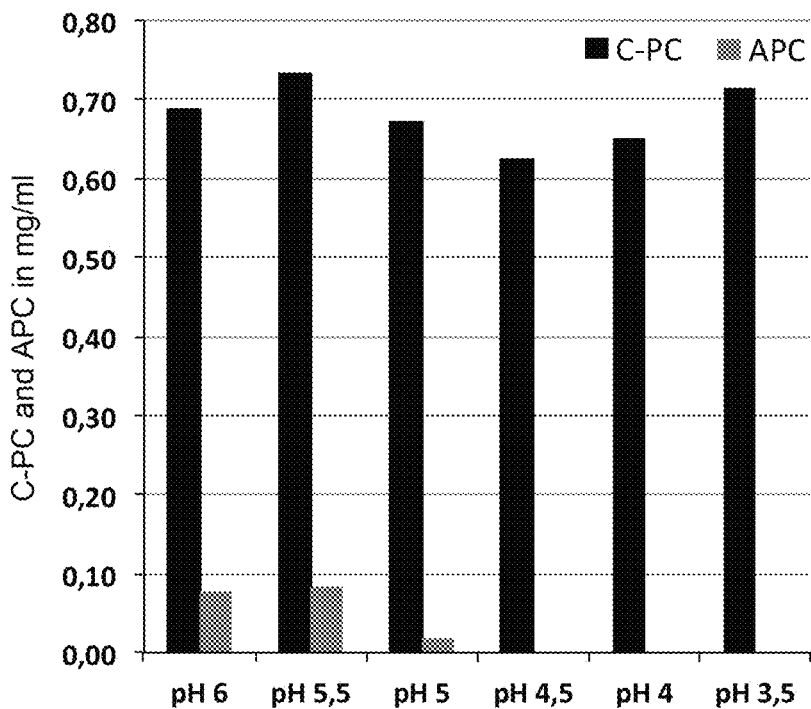
FIG. 5: Measurement of the concentration of C-PC and APC in different crude extracts obtained by centrifugation of a lysate of freeze-dried and rehydrated cells at different pH levels. APC concentrations (mg/ml) are shown in grey and C-PC concentrations (mg/ml) in black.

As previously described in Example 1, we can see an increase in the purity index correlated with a decrease in pH (FIG. 4). In this case, too, acidification also results in better separation of the liquid and solid phases and a pellet of cell debris and proteins which is more compact and easier to separate from the aqueous phase. Similar to what was observed in Example 1, APC is found in the pellet and not in the aqueous phase (FIG. 5) for pH values below 5. For pH values between 6 and 5, the amount of APC decreases in the supernatant as the pH decreases.

Example 3. Purification and Concentration of C-PC by Tangential Filtration

Figure 6:
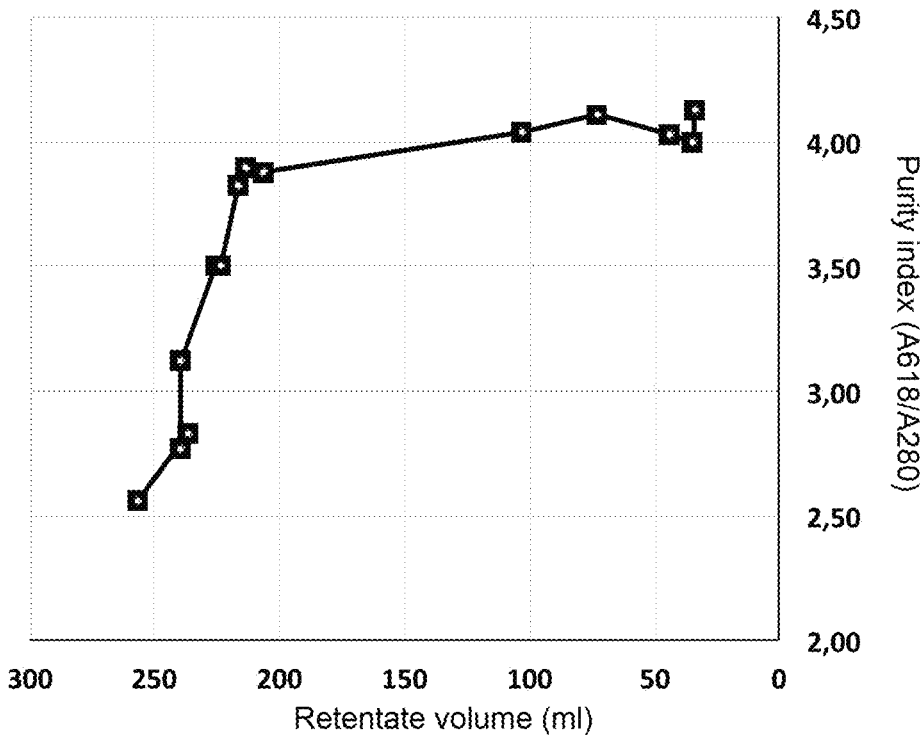
FIG. 6. Purification and concentration of C-PC by tangential filtration. The crude extract previously purified by precipitation at acid pH is filtered using a hollow-fibre system.
Figure 7:
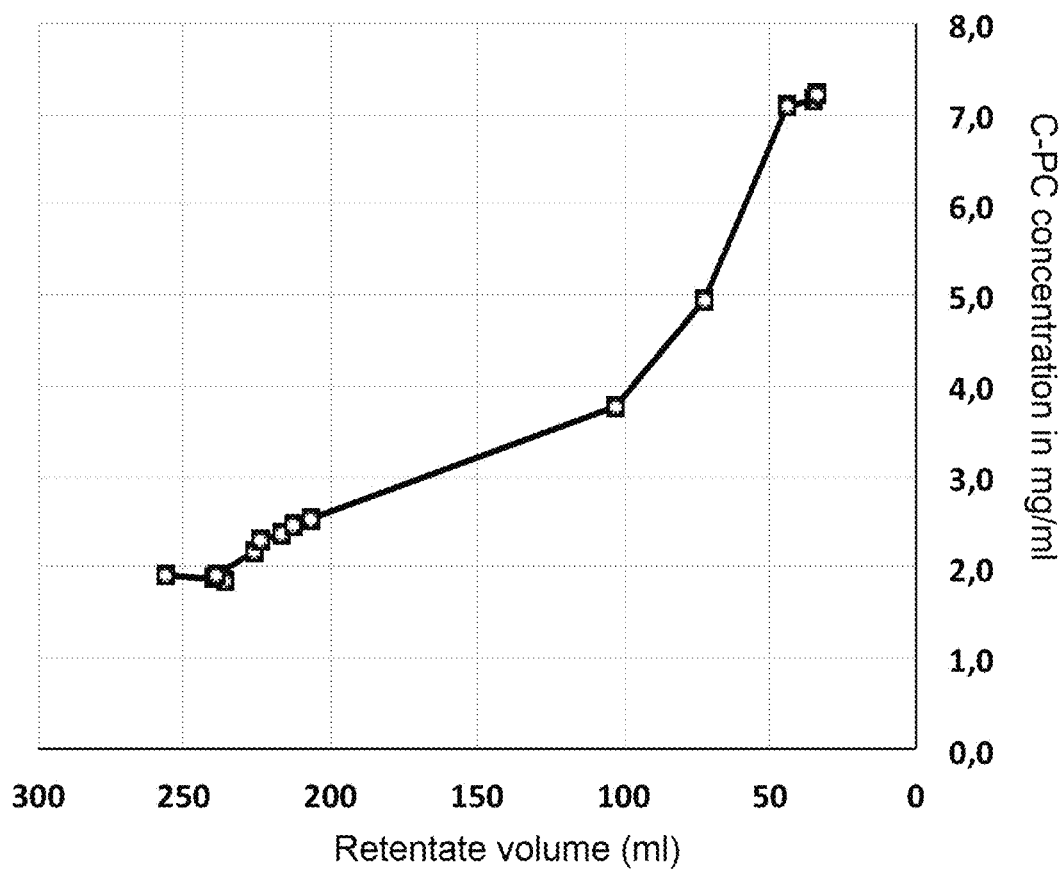
FIG. 7. Increase in C-PC concentration in the retentate during hollow-fibre filtration.

The crude extract after acid precipitation and centrifugation is filtered on a hollow-fibre tangential filtration module. Filtration through this mesh removes some of the proteins other than C-PC and thus increase the purity index (FIG. 6). The purity index that can be achieved by this method approaches the values normally obtained by much more complex methods involving biphasic extractions, or precipitation with ammonium sulphate, or even chromatography methods (Soresen et al., 2013; Cruz de Jesus et al., 2006). In parallel with the purification process, this filtration step removes the water from the C-PC extract (FIG. 7) and facilitates the subsequent drying of the product.

REFERENCES

Cruz de Jesús et al., "Methods for Extraction, Isolation and Purification of C-phycocyanin: 50 years of Research in Review" (2016) Int J Food Nutr Sci 3(3): 1-10.

Eisele et al., "Studies on C-phycocyanin from *Cyanidium caldarium*, a eukaryote at the extremes of habitat" Biochemica et Biophysica Acta 1456 (2000) 1456, 2-3, 99-107.

Eriksen N T. "Production of phycocyanin—a pigment with applications in biology, biotechnology, foods and medicine" Appl Microbiol Biotechnol. 2008 August; 80(1):1-14.

Kao et al., "Physical-chemical properties of C-phycocyanin isolated from an acido-thermophilic eukaryote, *Cyanidium caldarium*" Biochem. J. (1975) 147, 63-70

Myounghoon et al. "Isolation and Characterization of Thermostable Phycocyanin from *Galdieria Sulphuraria*," Korean journal of chemical engineering, 31 (2014): 1-6.

Sørensen et al. "Purification of the photosynthetic pigment C-phycocyanin from heterotrophic *Galdieria sulphuraria*" J Sci Food Agric. 2013 September; 93(12):2933-8

WO 2005/065697, WO 2015/090697, WO 2016/099261, WO 2017/050917, WO 2017/050918 et PCT/EP2016/079325 filed on 30 Nov. 2016

The invention claimed is:

1. A method for purifying acid-pH-resistant phycocyanins from a crude extract of acid-pH-resistant phycocyanins from cells of a phycocyanin-producing microorganism, said microorganism being of the genus *Galdieria*, said acid-pH-resistant phycocyanins being phycocyanins stable at a pH less than 5, and
    wherein the method comprises the steps of:
    a) adjusting the pH of the crude extract of acid-pH-resistant phycocyanins to a pH below 5 so as to precipitate organic matter other than acid-pH-resistant phycocyanins,
    b) recovering the supernatant comprising acid-pH-resistant phycocyanins obtained in step a) and
    c) isolating acid-pH-resistant phycocyanins from the supernatant of step b).

2. The method according to claim 1, wherein the acid-pH-resistant phycocyanin comprises a mixture of C-phycocyanin (C-PC) and allophycocyanin (APC), the C-PC/APC molar ratio being at least 5.

3. The method according to claim 1, wherein the acid-pH-resistant phycocyanins comprise at least 95 mol % acid-pH-resistant C-PC and less than 5 mol % APC, the percentages being expressed in relation to the total sum of APC and C-PC.

4. The method according to claim 1, wherein the recovery of the supernatant is carried out by filtration.

5. The method according to claim 1, wherein the microorganism is of the strain *Galdieria sulphuraria*.

6. The method according to claim 1, wherein residual acid-pH resistant phycocyanins contained in the precipitate of step a) are solubilized in an aqueous solution of acid pH 5 and separated from organic matter other than acid-pH-resistant phycocyanins and isolated by repeating steps b) and c).

* * * * *

SEQUENCE LISTING

<160> NUMBER OF SEQ ID NOS: 4

<210> SEQ ID NO 1
<211> LENGTH: 162
<212> TYPE: PRT
<213> ORGANISM: Galderia sulphuraria

<400> SEQUENCE: 1

```
Met Lys Thr Pro Ile Thr Glu Ala Ile Ala Ala Asp Asn Gln Gly
1               5                   10                  15

Arg Phe Leu Ser Asn Thr Glu Leu Gln Ala Val Asn Gly Arg Tyr Gln
            20                  25                  30

Arg Ala Ala Ala Ser Leu Glu Ala Ala Arg Ser Leu Thr Ser Asn Ala
        35                  40                  45

Gln Arg Leu Ile Asn Gly Ala Ala Gln Ala Val Tyr Ser Lys Phe Pro
    50                  55                  60

Tyr Thr Ser Gln Met Pro Gly Pro Gln Tyr Ala Ser Ser Ala Val Gly
65                  70                  75                  80

Lys Ala Lys Cys Ala Arg Asp Ile Gly Tyr Tyr Leu Arg Met Val Thr
                85                  90                  95

Tyr Cys Leu Val Val Gly Gly Thr Gly Pro Met Asp Glu Tyr Leu Ile
            100                 105                 110

Ala Gly Leu Glu Glu Ile Asn Arg Thr Phe Asp Leu Ser Pro Ser Trp
        115                 120                 125

Tyr Val Glu Ala Leu Asn Tyr Val Lys Ser Asn His Gly Leu Ser Gly
    130                 135                 140

Gln Ala Ala Asn Glu Ala Asn Thr Tyr Ile Asp Tyr Ala Ile Asn Ala
145                 150                 155                 160

Leu Ser
```

<210> SEQ ID NO 2
<211> LENGTH: 172
<212> TYPE: PRT
<213> ORGANISM: Galderia sulphuraria

<400> SEQUENCE: 2

```
Met Leu Asp Ala Phe Ala Lys Val Val Ala Gln Ala Asp Ala Arg Gly
1               5                   10                  15

Glu Phe Leu Ser Asn Thr Gln Leu Asp Ala Leu Ser Lys Met Val Ser
            20                  25                  30

Glu Gly Asn Lys Arg Leu Asp Val Val Asn Arg Ile Thr Ser Asn Ala
        35                  40                  45

Ser Ala Ile Val Thr Asn Ala Ala Arg Ala Leu Phe Ser Glu Gln Pro
    50                  55                  60

Gln Leu Ile Gln Pro Gly Gly Asn Ala Tyr Thr Asn Arg Arg Met Ala
65                  70                  75                  80

Ala Cys Leu Arg Asp Met Glu Ile Ile Leu Arg Tyr Val Ser Tyr Ala
                85                  90                  95

Ile Ile Ala Gly Asp Ser Ser Val Leu Asp Asp Arg Cys Leu Asn Gly
            100                 105                 110

Leu Arg Glu Thr Tyr Gln Ala Leu Gly Val Pro Gly Ala Ser Val Ala
        115                 120                 125

Val Gly Val Glu Lys Met Lys Asp Ser Ala Ile Ala Ile Ala Asn Asp
    130                 135                 140

Pro Ser Gly Ile Thr Thr Gly Asp Cys Ser Ala Leu Met Ala Glu Val
145                 150                 155                 160

Gly Thr Tyr Phe Asp Arg Ala Ala Thr Ala Val Gln
                165                 170
```

<210> SEQ ID NO 3
<211> LENGTH: 163
<212> TYPE: PRT
<213> ORGANISM: Galderia sulphuraria

<400> SEQUENCE: 3

```
Met Ser Leu Ile Ser Gln Ile Ile Asn Thr Ala Asp Glu Glu Leu Arg
1               5                   10                  15

Tyr Pro Asn Gly Gly Glu Leu Ser Thr Leu Ile Tyr Phe Phe Asn Thr
            20                  25                  30

Ala Asn Thr Arg Ile Asn Ile Ile Asn Lys Leu Lys Glu Arg Glu Lys
        35                  40                  45

Asp Ile Ile Gln Asn Ala Ser Lys Lys Leu Phe Gln Leu His Pro Glu
    50                  55                  60

Tyr Val Ser Ser Gly Gly Asn Ala Ser Gly Pro Lys Gln Arg Ala Leu
65                  70                  75                  80

Cys Leu Arg Asp Tyr Gly Trp Tyr Leu Arg Leu Val Thr Tyr Gly Ile
                85                  90                  95

Leu Ala Gly Asp Ile Thr Pro Ile Glu Lys Ile Gly Ile Ile Gly Val
            100                 105                 110

Lys Asp Met Tyr Asn Ser Leu Gly Val Pro Ile Ile Gly Met Tyr Asp
        115                 120                 125

Ala Ile Lys Cys Leu Lys Glu Ala Ser Ile Asn Ile Phe Glu Leu Ser
    130                 135                 140
```

```
Glu Glu Lys Asp Leu Ile Ile Pro Tyr Phe Asp Tyr Leu Ser Asn Ala
145                 150                 155                 160

Ile Leu Ser

<210> SEQ ID NO 4
<211> LENGTH: 253
<212> TYPE: PRT
<213> ORGANISM: Galderia sulphuraria

<400> SEQUENCE: 4

Met Ser Ile Val Thr Lys Ser Ile Val Asn Ala Asp Ala Glu Ala Arg
1               5                   10                  15

Tyr Leu Ser Pro Gly Glu Leu Asp Arg Ile Lys Ser Phe Val Leu Ser
                20                  25                  30

Gly Gln Arg Arg Leu Arg Ile Ala Gln Ile Leu Thr Asp Asn Arg Glu
            35                  40                  45

Arg Ile Val Lys Gln Ala Gly Gln Gln Leu Phe Gln Gln Arg Pro Asp
50                  55                  60

Ile Val Ser Pro Gly Gly Asn Ala Tyr Gly Glu Met Thr Ala Thr
65                  70                  75                  80

Cys Leu Arg Asp Leu Asp Tyr Tyr Leu Arg Leu Val Thr Tyr Gly Val
                85                  90                  95

Val Ala Gly Asp Ile Ser Pro Ile Glu Glu Ile Gly Leu Glu Asp Phe
                100                 105                 110

Met Gln Asp Ala Ile Thr Ala Val Ile Asn Thr Ala Asp Val Gln Gly
                115                 120                 125

Lys Tyr Leu Asp Asn Ser Ser Ile Glu Lys Leu Lys Gly Tyr Phe Gln
130                 135                 140

Thr Gly Glu Leu Arg Val Arg Ala Ala Thr Ile Ala Ala Asn Ala
145                 150                 155                 160

Ala Gly Ile Ile Lys Asp Ala Val Ala Lys Ser Leu Leu Tyr Ser Asp
                165                 170                 175

Ile Thr Arg Pro Gly Gly Asn Met Tyr Thr Thr Arg Arg Tyr Ala Ala
                180                 185                 190

Cys Ile Arg Asp Leu Asp Tyr Tyr Leu Arg Tyr Ala Thr Tyr Ser Met
            195                 200                 205

Leu Ala Gly Asp Pro Ser Ile Leu Asp Glu Arg Val Leu Asn Gly Leu
        210                 215                 220

Lys Glu Thr Tyr Asn Ser Leu Gly Val Pro Ile Gly Ala Thr Ile Gln
225                 230                 235                 240

Ser Ile Gln Ala Met Lys Glu Val Thr Ser Ser Leu Val
                245                 250
```